United States Patent [19]

Suzuki

[11] Patent Number: 5,530,493
[45] Date of Patent: Jun. 25, 1996

[54] OPHTHALMIC INSTRUMENT CAPABLE OF ADJUSTING THE QUANTITY OF ILLUMINATION BASED ON THE SENSITIVITY OF THE FINDER SYSTEM

[75] Inventor: Koichi Suzuki, Yokohama, Japan

[73] Assignee: Nikon Corporation, Tokyo, Japan

[21] Appl. No.: 373,460

[22] Filed: Jan. 17, 1995

Related U.S. Application Data

[63] Continuation of Ser. No. 161,434, Dec. 6, 1993, abandoned, which is a continuation of Ser. No. 853,255, Mar. 18, 1992, abandoned.

[30] Foreign Application Priority Data

Mar. 28, 1991 [JP] Japan .................. 3-019295 U

[51] Int. Cl.⁶ ............................................. A61B 3/14
[52] U.S. Cl. ........................ 351/206; 351/221; 351/245
[58] Field of Search ................................. 351/206, 245, 351/221; 354/62, 79, 145.1

[56] References Cited

U.S. PATENT DOCUMENTS

| | | | |
|---|---|---|---|
| 3,944,342 | 3/1976 | Martinez | 351/206 |
| 4,018,514 | 4/1977 | Plummer | 351/206 |
| 4,149,787 | 4/1979 | Kobayashi et al. | 354/62 |
| 4,208,107 | 6/1980 | Oharek | 351/206 |
| 4,429,970 | 2/1984 | Fujiwara | 351/206 X |
| 4,573,786 | 3/1986 | Taniguchi et al. | 354/145.1 X |
| 4,580,885 | 4/1986 | Takahashi | 354/62 |
| 4,669,836 | 6/1987 | Richardson et al. | 351/206 |
| 4,692,003 | 8/1987 | Adachi et al. | 351/212 |
| 4,820,039 | 4/1989 | Ahmad | 351/206 X |
| 4,834,526 | 5/1989 | Nunokawa | 351/206 |
| 4,912,499 | 3/1990 | Desormeaux | 354/145.1 X |
| 5,118,179 | 6/1992 | Sano et al. | 351/206 |
| 5,146,250 | 9/1992 | Sakamoto et al. | 354/145.1 |

*Primary Examiner*—William L. Sikes
*Assistant Examiner*—Hung Xuan Dang
*Attorney, Agent, or Firm*—Shapiro and Shapiro

[57] ABSTRACT

An ophthalmologic instrument includes a body of the instrument including an objective optical system and a processing unit, and a camera section including a camera and a second processing unit and interchangeably mounted on the body of the instrument. The first processing unit and the second processing unit are communicably connected together by a predetermined form of serial data communication. In a mode of the invention, an auxiliary processing unit for controlling the operation of the camera is provided in the camera section. The auxiliary processing unit and the second processing unit are connected together so as to be able to exchange information.

3 Claims, 7 Drawing Sheets

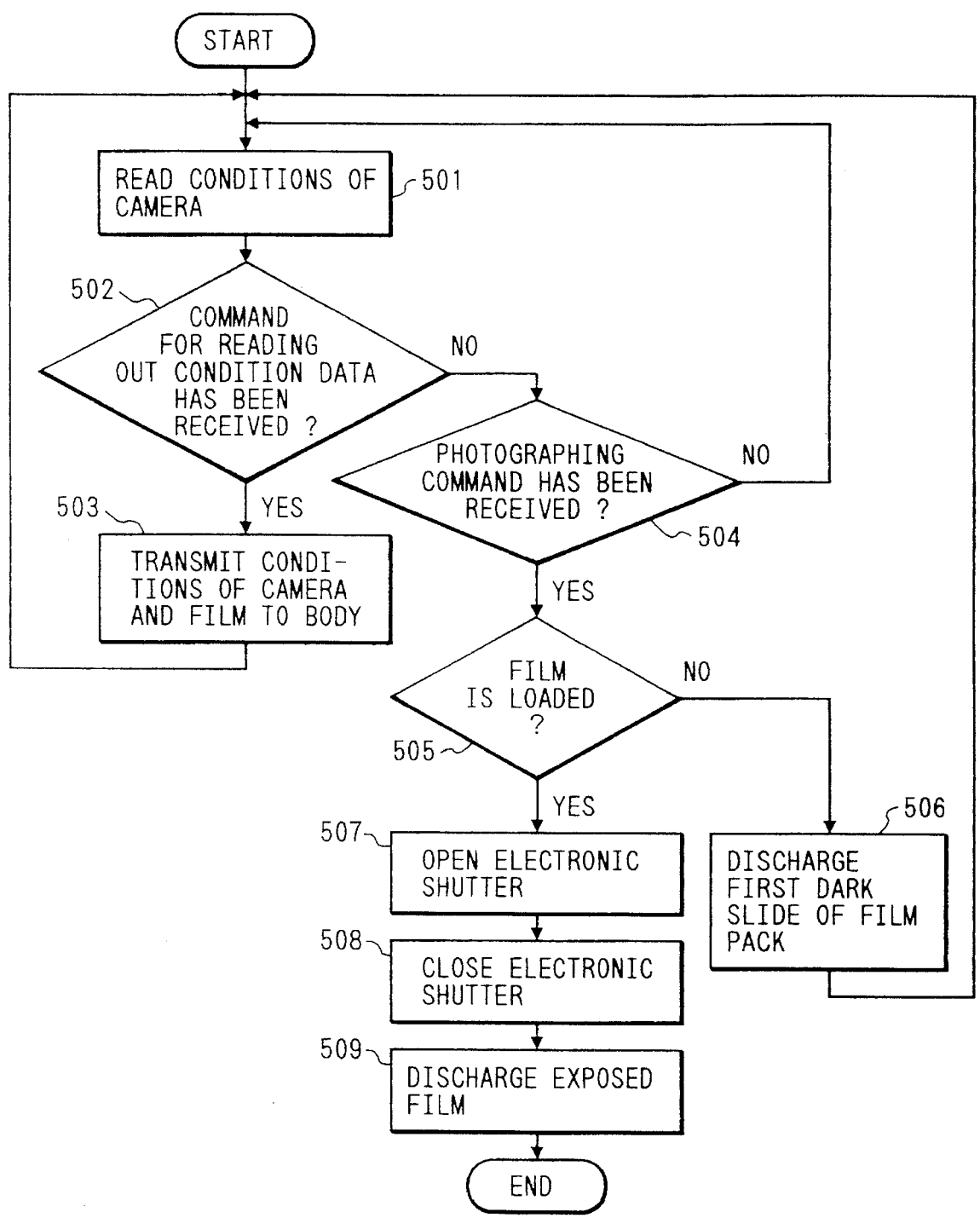

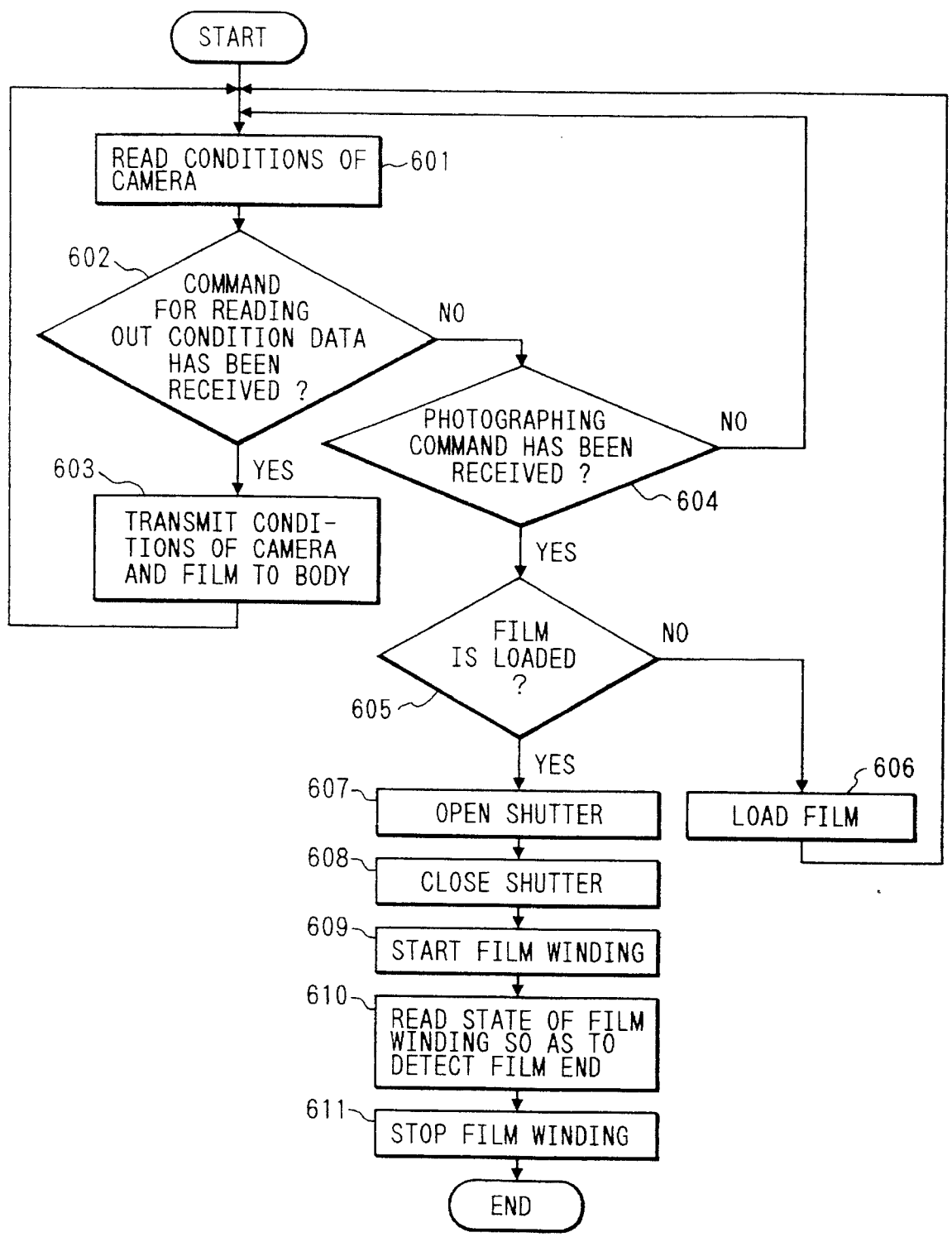

OPHTHALMIC INSTRUMENT CAPABLE OF ADJUSTING THE QUANTITY OF ILLUMINATION BASED ON THE SENSITIVITY OF THE FINDER SYSTEM

This is a continuation of application Ser. No. 08/161,434 filed Dec. 6, 1993 now abandoned, which is a continuation of application Ser. No. 07/853,255 filed Mar. 18, 1992, both now abandoned.

BACKGROUND OF THE INVENTION

1. Field of the Invention

This invention relates to an ophthalmologic instrument interchangeably provided with various cameras.

2. Related Background Art

A prior-art ophthalmologic instrument, for example, an eye fundus camera, is comprised of a body of the instrument including a power source, and a removable camera section. In some cases, a power source section is provided discretely from the body. There are a plurality of kinds of camera instruments such as one having a 35 mm camera, one having an instant camera, and one having a television camera, and they are interchangeable.

As the removable camera section of an ophthalmologic instrument, there is a 35 mm camera, an instant camera or the like. These cameras each have an electrical contact on a camera mount, and may be directly electrically connected by the camera mount, or only an electrical signal may be taken out by a cable and the camera may be connected by a discretely provided connector instead of the camera mount.

The kinds of signals differ depending on a camera section connected. The same signals can share an electrical contact between a plurality of camera sections, but in the case of signals incompatible with each other, it is necessary to provide a contact discretely. This has led to the problem that the number of the contacts of the camera mount is increased. There has also been the problem that there is a limit in the number of contacts provided on the camera mount and a greater number of contacts results in a smaller size of the contacts and a higher possibility of unsatisfactory contact occurring.

As a countermeasure for decreasing the number of the contacts of the camera mount to eliminate such problems, there has been adopted a method of changing a terminal for reading out the state of the camera section from binary one representing the ON/OFF of a switch to one in which for example, a change occurs stepwise from 0 V to 5 V, thereby reducing the number of terminals to one. For example, the conditions regarding film, such as film unloaded condition, film loaded condition and film end, have been divided into several voltage levels, whereby the information of the camera section side has been transmitted to a power source section or a body.

Here, an eye fundus camera will be described somewhat in detail.

In an ophthalmologic instrument such as an eye fundus camera or a slit lamp, observation or photographing is effected while a plurality of camera sections are interchanged. Therefore, a color photographing 35 mm camera, a monochromatic photographing 35 mm camera, a color photographing instant camera 1, a color photographing instant camera 2, a color photographing instant camera 3, a monochromatic photographing instant camera, etc. are connected to a camera mount.

During photographing, it is necessary that a power source section and a body determine a quantity of flash fit for the camera section thereof and effect an operation fit for the camera section.

Several parameters are concerned in the determination of the quantity of flash. These parameters include, for example, film speed, the size of the image on the film, photographing angle of view, the type of a filter used during photographing, photographing region, and correction by an exposure correction switch or the like.

In the prior-art eye fundus camera, the instrument has automatically determined the quantity of flash in accordance with pre-programmed conditions (the type of the camera, the set value of film speed SW, the state of the instrument, etc.)

Also, the service life of an ophthalmologic instrument such as an eye fundus camera or a slit lamp is relatively long and therefore, it is often the case that after the sale of products, the machine parts of available camera sections are newly announced. Recently, the requirement for the photographing by electronic still cameras and television cameras has risen and the types of interchangeable camera sections have been on the increase. This has become active in connection with image processing.

In an ophthalmologic instrument such as an eye fundus camera, the optical path changes during observation and during photographing. The optical path during observation terminates at an eyepiece finder and is temporarily changed over to the camera section side only during photographing. That is, the usual optical path terminates at the eyepiece finder.

Therefore, the examiner sets the quantity of light of an observation illumination lamp so that the brightness of the fundus of the examinee's eye observed through the eyepiece finder may be brightness ready to be observed under conditions such as a certain angle of view, a certain filter and a certain diameter of pupil. After once set, the eye fundus camera is designed to automatically control the quantity of observation illumination light in conformity with the various conditions so that the brightness of the fundus of the eye seen through the eyepiece finder may be constant even if an angle of view switching switch, a filter switch, a pupil diameter switching switch, etc. are operated.

Data to be imprinted simultaneously with the image of the fundus of the eye during the photographing of the fundus of the eye is displayed within the eyepiece finder. There are a handwritten data display section for imprinting the examinee's name and information to be preserved as some memorandum and an LED display section available as the clinical chart number, the date of photographing, the number of a group examination, etc. Also, an eye fundus camera having the automatic focusing function has an AF indicator display section for displaying the focused state.

Further, when the image of the fundus of the eye is to be observed with naked eye through the eyepiece finder of the eye fundus camera, the quantity of observation illumination light is set under predetermined conditions as described above, whereby the eye fundus camera controls the quantity of observation illumination light in conformity with said conditions even if said conditions are changed and therefore, the examiner has been able to concentrate on the observation of the image of the fundus of the eye.

However, when the image of the fundus of the eye is to be observed by the use of a television camera, the television camera is connected as a camera section to a camera mount. Thus, the examiner does not observe the image of the fundus of the eye through the eyepiece finder, but observes the image of the fundus of the eye on a CRT screen. However, under the existing circumstances, the image of the fundus of the eye obtained through the eyepiece finder is better in the confirmation of the presence or absence of flare, the resolving power, etc. than that on the CRT screen and therefore, it is observed (as an electronic finder) and photographed (as a television camera device) with the eyepiece finder and the television camera device section changed over.

In the prior art as described above, to decrease the number of the contacts of the camera mount, there is conceivable a method of increasing the number of the steps of a voltage on a signal line, and transmitting a plurality of kinds of information by a signal line. Such a method is not impossible, but is difficult because a great number of steps of a voltage becomes necessary as the kinds of information increase.

Accordingly, it has been impossible to decrease the number of the contacts of the camera mount very much. It has also been impossible to transmit a lot of information even if there is a great number of contacts.

Thus, to obtain a plurality of kinds of information from the camera section, the prior-art method has suffered from a problem.

Also, there are many kinds of camera sections and a film speed setting switch cannot be provided for each camera section and therefore, camera sections of similar kinds set the film speed by one and the same film speed setting switch. This has led to the necessity of re-setting the film speed of the power source section or the body during the interchange of the camera section which serves also as a film speed setting switch. If the user forgets to re-set the film speed, it will become impossible to photograph at proper exposure. Further, an eye fundus camera is used in a state relatively approximate to a dark room and therefore, there has been the problem that when operating a certain film speed setting switch, the user changes another film speed setting switch by mistake. On the other hand, the provision of film speed setting switches corresponding to all camera sections on the power source section or the body results in the presence of too many switches, which has apparently made the instrument difficult to use.

In the prior-art eye fundus camera, the camera section has been directly controlled through the camera mount from the power source section or the body and therefore, it has been necessary to modify the base plate of the power source section or the body or add an interface to the outside in order to take an interface with a new camera section.

Particularly, image processing apparatuses using an eye fundus camera or a slit lamp as an input device differ in interface specification from maker to maker and therefore, it is difficult to modify the base portion of the power source section or the body to thereby cope with numerous camera sections. In the external interface, the camera section is separate from the body and this has led to the problem that the camera section cannot be interchanged by one touch.

Also, the data to be imprinted simultaneously with the image of the fundus of the eye is displayed within the eyepiece finder of the eye fundus camera, as previously described.

These display sections are disposed around the finder and during observation, what one consciously sees can be seen well and thus, it has not posed so great a problem that the display sections are a little too bright. Therefore, the quantity of light in the display sections has been constant when the optical path is on the eyepiece finder side. Only during photographing, the quantity of light has been varied in conformity with the film speed or the size of the image on the film. Nevertheless, during fluorescence photographing, the image of the fundus of the eye is hardly seen, and this has led to the problem that the fundus of the eye becomes difficult to see when the quantity of light for displaying the data is a little too bright.

Further, when the image of the fundus of the eye is to be observed by the use of a television camera, the television camera is connected as a television camera section to the camera mount, but there is a difference between the sensitivity of a naked eye and the sensitivity of the television camera, and this has led to the problem that the quantity of observation illumination light must be re-set each time the optical path is changed over between the eyepiece finder and the television camera section.

That is, in the prior art, the control system of the camera section and the quantity of flash during photographing become necessary as the parameters of each of various camera sections.

Television cameras differ in sensitivity depending on whether the image pickup element used therein is a solid state image pickup element or an image pickup tube or a photomultiplier and further, depending on the area of the image pickup element and one-element or three-element construction and therefore, television camera sections differ in sensitivity depending on the kinds thereof. The sensitivity of the naked eye is irregular from person to person. Thus, there has also been the problem that it is necessary to take the corrected value of the difference in sensitivity between the naked eye irregular in sensitivity and the television camera section.

Further, to photograph the image of the fundus of the eye by a television camera or the like, the image of the fundus of the eye and the data system display sections (the handwritten data display section, the LED display section and the AF indicator display section) are photographed completely at one time. Since the television camera cannot consciously select an image as the naked eye does, the data system display sections are photographed at the same sensitivity. This has led to the problem that particularly during fluorescence photographing, those display sections are too bright and the image field becomes difficult to see.

SUMMARY OF THE INVENTION

The present invention has been made in view of the above-noted problems peculiar to the prior art, and an object thereof is to provide an ophthalmologic instrument which can readily cope with the kinds of camera equipment which continue to be increased by the development of technology and the resultant various specifications.

According to the present invention, there is provided an opthalmologic instrument comprising:

a body of the instrument including an objective optical system and first control means;

a camera section including camera means and second control means, the section being interchangeably mounted on the body of the instrument; and connecting means for communicably connecting the first control means and the second control means together by a predetermined form of serial data communication.

As described above, the control means of the body and the control means of the camera section are connected together so as to be capable of effecting serial data communication therebetween and therefore, a remote command from the body and data sent from the camera section to the body can be digitalized. That is, the command and data can be given and taken by a digital signal and therefore, very complicated exchange of signals can be effected even by a few contacts. The contact construction of a camera mount in an embodiment described later includes a power source line, a return line, a synchronous type clock line, a synchronous type input data line, a synchronous type output data line, an x contact line and a connection state line.

Also, if film speed setting means are individually provided in the camera section, not only what kind of camera is connected to the power source section or the body, but also the speed of film loaded in the camera and the state of the camera can be known by serial communication through a camera mount simply by detaching the camera section from the camera mount and interchanging another camera section on the camera mount.

If camera control means is further provided in the camera section and in addition, a communication procedure format is prepared, the camera section can operate a camera part by a command from the power source or the body.

Also, the interface specification of the power source section and the camera section can be constructed of the power source line and the serial communication line as previously described and therefore, the camera section added later can be connected to the power source section and the body if it only satisfies this interface specification. Since the camera control means is disposed in the camera section and is controlled by the CPU of the camera section, the driving of the camera device can be programmed in conformity with the characteristic thereof and thus, the modification of the base board of the power source section and the body becomes unnecessary. The interface with the camera device heretofore assumed with the power section or the body can be assumed between a camera section made intelligent and the camera device, and the connection to the body can be accomplished by only the camera mount contact. Accordingly, the connection to the body can be accomplished by one touch.

BRIEF DESCRIPTION OF THE DRAWINGS

FIG. 6 is a flow chart illustrating the operation of an instant camera.

FIG. 7 is a flow chart illustrating the operation of a 35 mm camera.

DETAILED DESCRIPTION OF THE PREFERRED EMBODIMENTS

An embodiment of the present invention will hereinafter be described with reference to the drawings. The ophthalmologic instrument of the present embodiment is an eye fundus camera.

Figure 1:
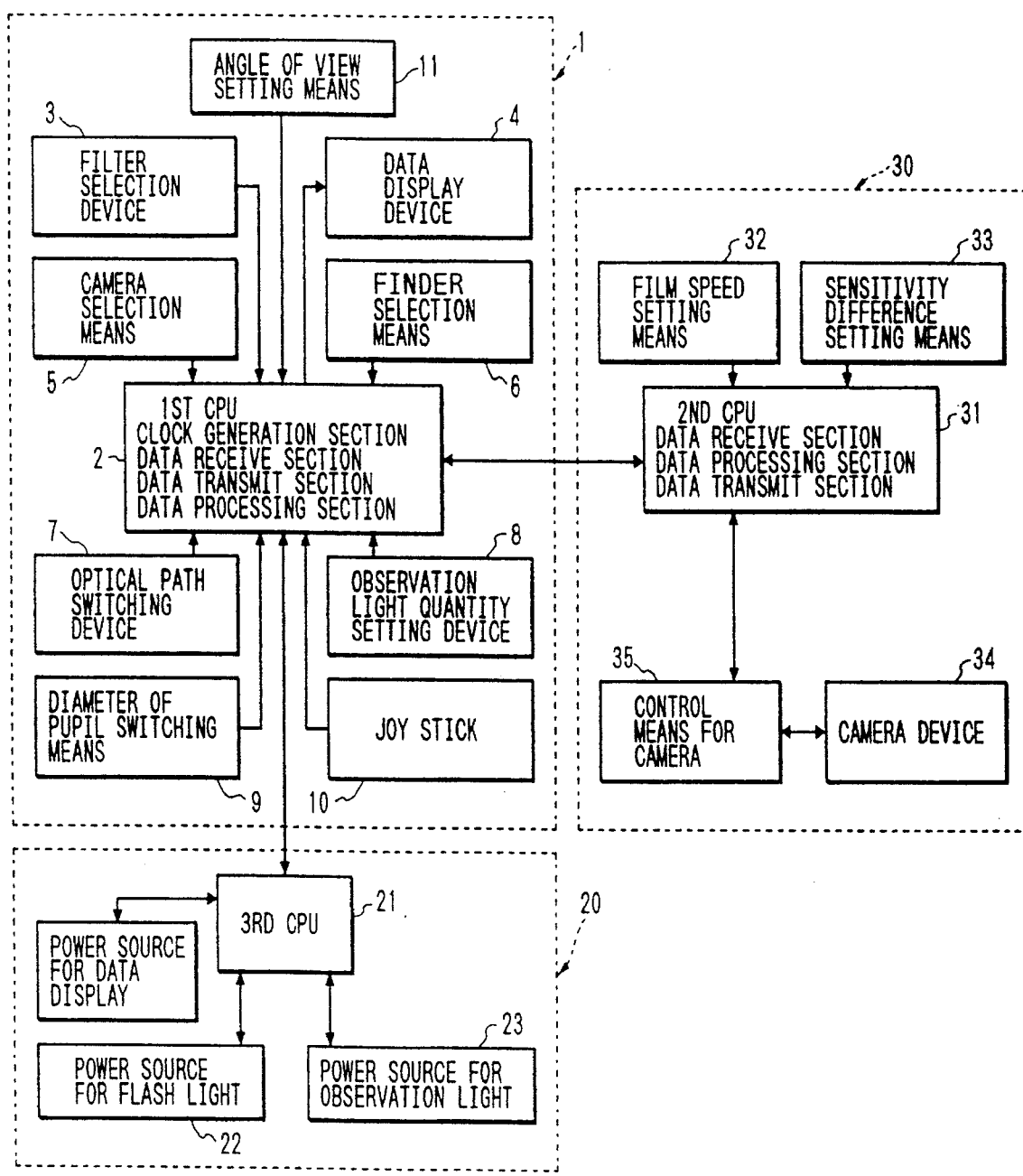
FIG. 1 is a block diagram showing the construction of an embodiment of the present invention.

Referring to FIG. 1 which is a block diagram showing the construction of the eye fundus camera, the reference numeral 1 designates a body, the reference numeral 30 denotes a camera section, and the reference numeral 20 designates a power source section. A first CPU 2 is contained in the body 1, a second CPU 31 is contained in the camera section 30, and a third CPU 21 is contained in the power source section 20. The first CPU 2 exchanges signals with the second CPU 31 and the third CPU 21 by communication. Consequently, the operation of I/O of each section is performed by the CPU of the each section.

The body 1 is provided with various filters for selecting the wavelength of observation illumination light, and also is provided with a filter selection device 3 capable of detecting filters disposed in an observation illumination optical path, a data display device 4 receiving the information of the kinds of the filters and capable of changing over the quantity of light of a data display section (a space provided on the marginal edge of the photographic angle of view), camera selection means 5 for designating camera sections connected to a plurality of camera mounts, angle of view selection means 11 for selecting the angle of view, finder selection means 6 for selecting an eyepiece finder or an electronic finder when a television camera is mounted, an optical path switching device 7 for switching an observation optical path and a photo-taking optical path depending on the purpose, an observation light quantity setting device 8 for setting the quantity of observation light in conformity with the kinds of the filters, a diameter of pupil switching device 9 for making the quantity of observation light correspond to the diameter of the examinee's pupil, and a joy stick 10 for switching on a joy stick switch to thereby cause a flash device to emit light and operate the body 1 and the camera section 30 on a base, not shown.

The camera section 30 is provided with film speed setting means 32 for outputting the information of film speed (the film speed of a television camera is the image pickup performance of the television camera as converted into the film speed of a 35 mm camera) when the television camera, like the 35 mm camera, is caused to flash stroboscopically to thereby photograph an image, sensitivity difference setting means 33 for setting the sensitivity difference between the eyepiece finder and the electronic finder by the television camera and provided with a sensitivity correction switch, a camera device 34, and camera control means 35 for taking the interface with the camera device 34 and outputting the information of the type of the camera and the state and type of the film to the second CPU.

The power source section 20 is provided with a power source 23 for observation light which controls and outputs so as to obtain a predetermined quantity of light in accordance with instructions based on the various kinds of information of the body 1 and the camera section 30 from the third CPU 21, and a power source 22 for flash light which charges and discharges in addition thereto.

The exchange of signals between the first CPU 2 and the second CPU 31 will now be described. This interface is comprised of a power source line and a serial communication line. In the present embodiment, the contact construction of the camera mount is seven-contact construction comprising a power source line, a return line, a synchronous type clock line, a synchronous type input data line, a synchronous type output data line, an x contact line and a connection state line.

However, where communication is effected by non-synchronous communication, the clock line becomes unnecessary. Also, where flash synchronization may be at a low speed, the x contact line becomes unnecessary. Further, if design is made to examine the connection state by communication, the connection line will be unnecessary. The data input/output line has its data transmission direction changeable over as required. Consequently, the minimum construction of the contact includes the power source line, the return line, the synchronous type clock line and the synchronous type input/output line. Alternatively, the minimum construction of the contact can be realized by the power source line, the return line, a non-synchronous type input data line and a non-synchronous type output data line.

Through the interface comprised of seven contacts as described above, the clock generating portion of the first CPU 2 outputs a clock corresponding to 8 bits in response to a transmission data command made into an 8-bit construction through the synchronous type clock line. In synchronism with this clock, a transmission data section transmits transmission data (for example, a command for reading out the state of the camera) through the synchronous type output line. The second CPU 31 which has received this transmission data by a reception data section reads out the state of the camera by a data processing section, and outputs the data thereof from the transmission data section of the second CPU 31 to the reception data section of the first CPU 2 through the synchronous type input data line. On the basis of that data, the data processing section of the first CPU 2 effects processing. A command is processed in this manner, and a plurality of commands from the first CPU 2 are processed by repeating the above-described operation.

Also, the first CPU 2 always monitors the connection state line. This line is designed such that the level of the signal thereof is varied by whether the camera section 30 is connected to the camera mount of the body. When a camera mount to which the camera section is not connected to selected by the camera selection means 5, the warning that no connection is effected is produced. When at that point of time, the switch of the joy stick 10 is input, the flashing of the flash device is prohibited. As in the prior art, the x contact line is used when the x contact is utilized.

The exchange of signals between the first CPU 2 and the third CPU 21 is effected by the interface of the power source line, the return line, the synchronous type clock line and the synchronous type input/output line, and serial communication is effected in a manner similar to that described previously.

Description will hereinafter be made of the operation, during photographing, of an embodiment of the ophthalmologic instrument of the present invention constructed as described above.

Figure 2:
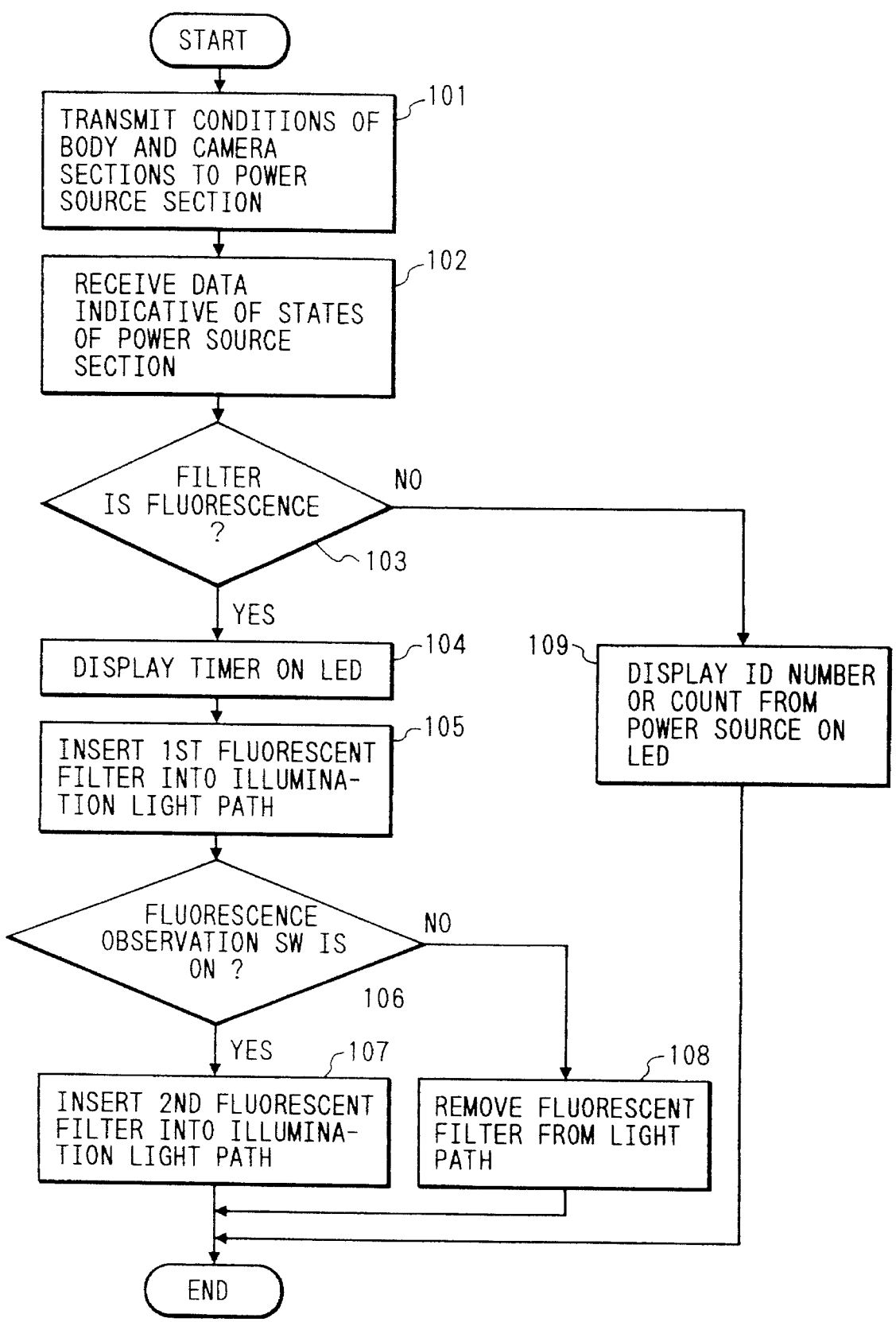
FIG. 2 is a flow chart illustrating an operation concerned with the observation in the present invention.

The operations of the body 1 and the power source section 20 will first be described with reference to flow charts. Referring to FIG. 2 which is a flow chart illustrating the operation concerned with observation, the first CPU 2 receives the information of the type of the camera designated by the camera selection means 5 and the angle of view selected by the angle of view selecting means 11, the information of the filter selected by the filter section device 3, the second fluorescent filter selection information (the fluorescent observation switch information), the diameter of pupil information from the diameter of pupil switching device 9 and the light quantity information of the observation light quantity setting device 8, and transmits the conditions of the body 1 and camera section 30 to the power source section 20 (step 101).

Here, the light quantity information of the observation light quantity setting device 8 refers to the light quantity information when the observation light has been set to brightness with which the examiner can readily observe an eye to be examined through the eyepiece finder under conditions of a certain angle of view, a certain filter (including the fluorescent filter and second fluorescent filter selection information) and a certain diameter of pupil.

The power source for observation light is controlled by the third CPU 21 so that the light quantity information of the observation light quantity setting device 8 may not vary and the brightness of the eye to be examined from the eyepiece finder may be constant even when such conditions as the angle of view, the filter, the diameter of pupil and the entry of the first and second fluorescent filters into the light path change.

The information of the second fluorescent filter does not become effective unless the fluorescent filter is selected by the filter selection device 3.

The third CPU 21 transmits the charged state of the power source 22 for flash light in the power source section, the displayed data of the data display section and other states of the power source section to the first CPU 2 and thus, the first CPU 2 acknowledges the state data of the power source section (step 102).

The third CPU 21 controls the power source for observation light so that the brightness of the eye to be examined from the eyepiece finder may be constant, in accordance with various kinds of information from the first CPU 2 (such as the angle of view, the filter, the diameter of pupil, the entry of the first and second fluorescent filters into the light path, and the light quantity information of the observation light quantity setting device 8).

The first CPU 2 judges whether the filter selected by the filter selection device 3 is a fluorescent filter or other filter (step 103), and if the filter selected is a fluorescent filter, a timer is displayed on the LED of the data display device (step 104). If the filter selected is other than the fluorescent filter, observation of other than fluorescence can be done and an ID number or count conforming to the setting of the power source section is displayed (step 109).

The power source section also has an LED of the data display device, and the third CPU 21 likewise judges and displays a timer, or displays an ID number or count.

When the first CPU 2 judges that the fluorescent filter is selected by the filter selection device 3 (step 103), it inserts the first fluorescent filter into the light path (step 105), and further inserts the second fluorescent filter into the light path (step 107) or removes it from the light path (step 108), by the second fluorescent filter selection information (step 106). By the second fluorescent filter being inserted into the light path, fluorescence observation becomes possible. Inserting the fluorescent filters into the light paths of the illuminating optical system and the observation optical system requires a greater quantity of light because the wavelength of the fluorescence of the image created upon reception of the illuminating light from the eye to be examined differs from that of the illuminating light. There is a case where the quantity of flash light is deficient because of the relation among the type of the camera and the film speed and the power source for flash light. In such case, the third CPU 21 gives warning to the examiner.

The third CPU 21 always monitors whether the power source for flash light is charged. The charged state of this power source is transmitted as one of state data to the first CPU. The third CPU 21 monitors also whether the power source for flash light completes charging within a predetermined time. When the charging time exceeds the predetermined time, the third CPU 21 judges that some trouble has occurred, and gives warning to the examiner.

Figure 3:
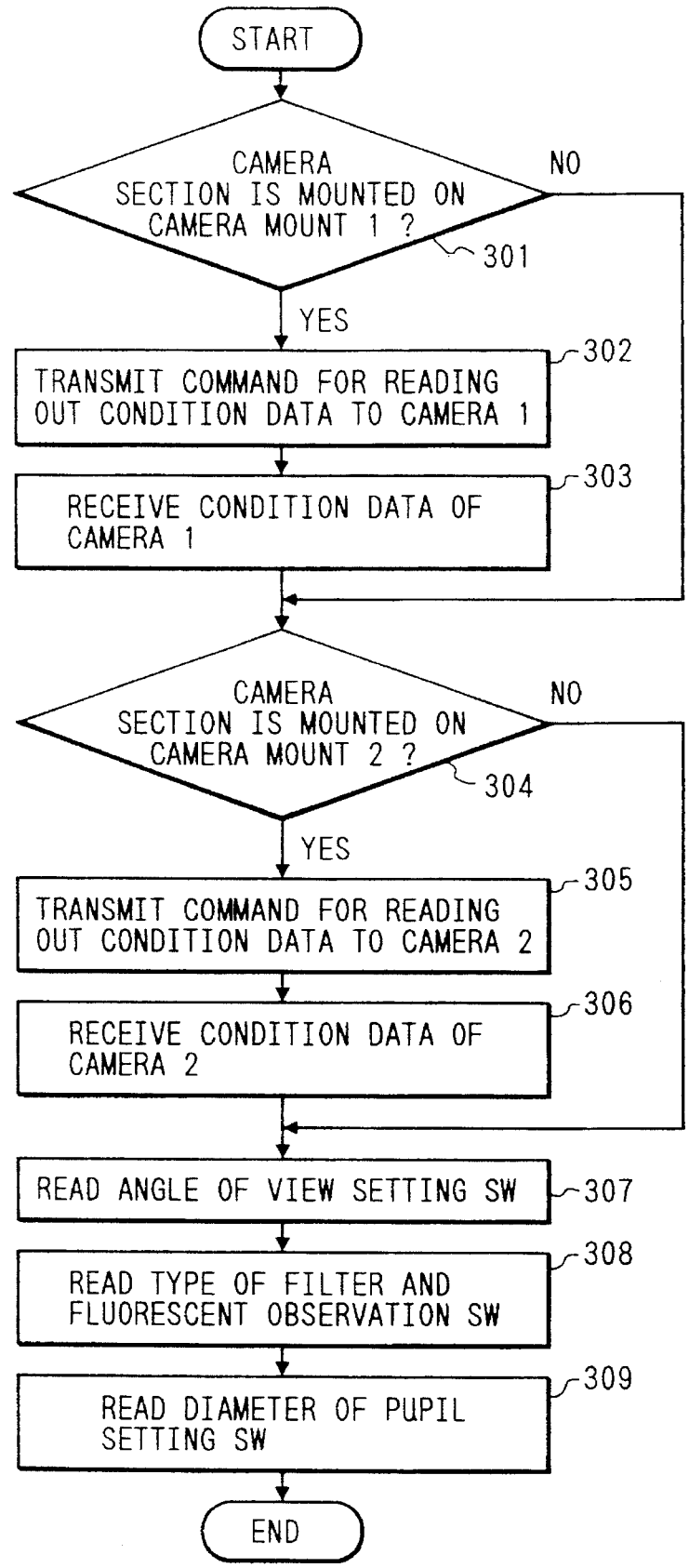
FIG. 3 is a flow chart illustrating an operation concerned with preparation for photographing in the present invention.

FIG. 3 is a flow chart of an operation concerned with preparation for photographing.

The mounted state of the camera section 30 is first confirmed. Whether the camera section 30 is mounted on the camera mount 1 (the portion in which the body and the camera section are connected together) is judged (step 301). If the camera section 30 is mounted, the first CPU 2 transmits a command for reading out the condition of the camera (i.e., the camera mounted on the camera mount 1) to the second CPU 31 of the camera section 30 (step 302). When in response to the command for reading out the condition of the camera 1, the second CPU 31 returns condition data such as the type of the camera 1 (a 35 mm camera, instant cameras 1, 2, . . . , television cameras 1, 2 . . . , etc.), the kind of the film (color film, monochromatic film, etc.) and the condition of the film (the film is not inserted, the film is not loaded, the film is inserted, the film end, etc.), the first CPU 2 receives and acknowledges the condition data of the camera 1 (step 303).

If the camera section 30 is not mounted on the camera mount, whether the camera section 30 is mounted on the camera 2 is judged (step 304). If the camera section 30 is mounted on the camera 2, the first CPU 2 transmits a command for reading out the condition of the camera 2 (i.e., the camera mounted on the camera mount 2) to the second CPU 31 of the camera section 30 (step 305). When the second CPU 31 returns the condition data of the camera, the first CPU 2 receives the condition data of the camera (step 306).

Thereafter, the setting switch of the camera selection means 5 is read (step 301 or step 304), the setting switch of the angle of view setting means 11 is read (step 307), and the type of the filter set on the filter selection device 3 and whether the observation is fluorescent observation are read (step 308). Also, the situation of the diameter of the pupil is input from the diameter of pupil switching device 9 (step 309). In this manner, the operation concerned with the preparation for photographing is completed.

Figure 4:
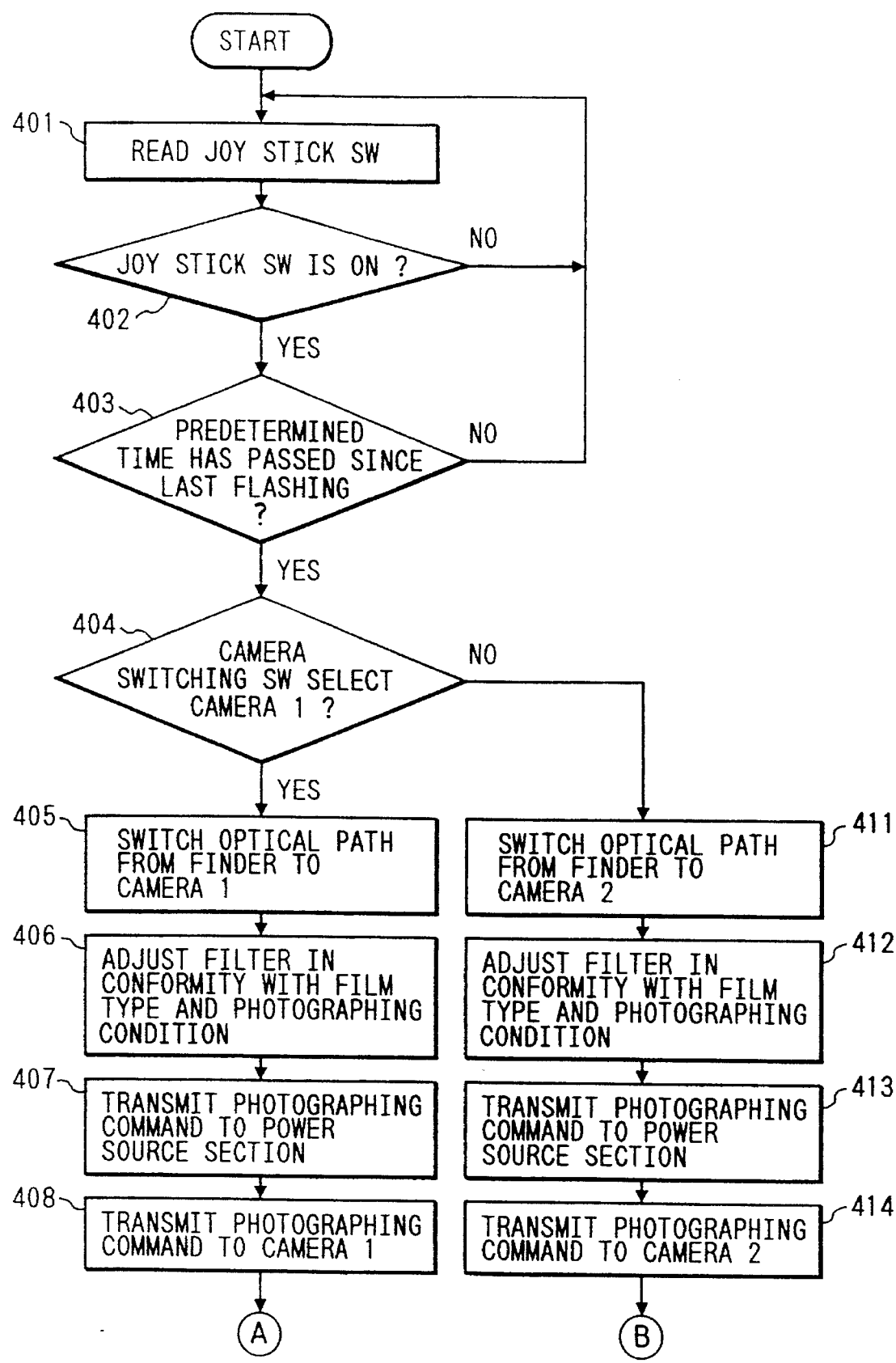
FIG. 4 is a flow chart illustrating an operation concerned with the photographing in the present invention.
Figure 5:
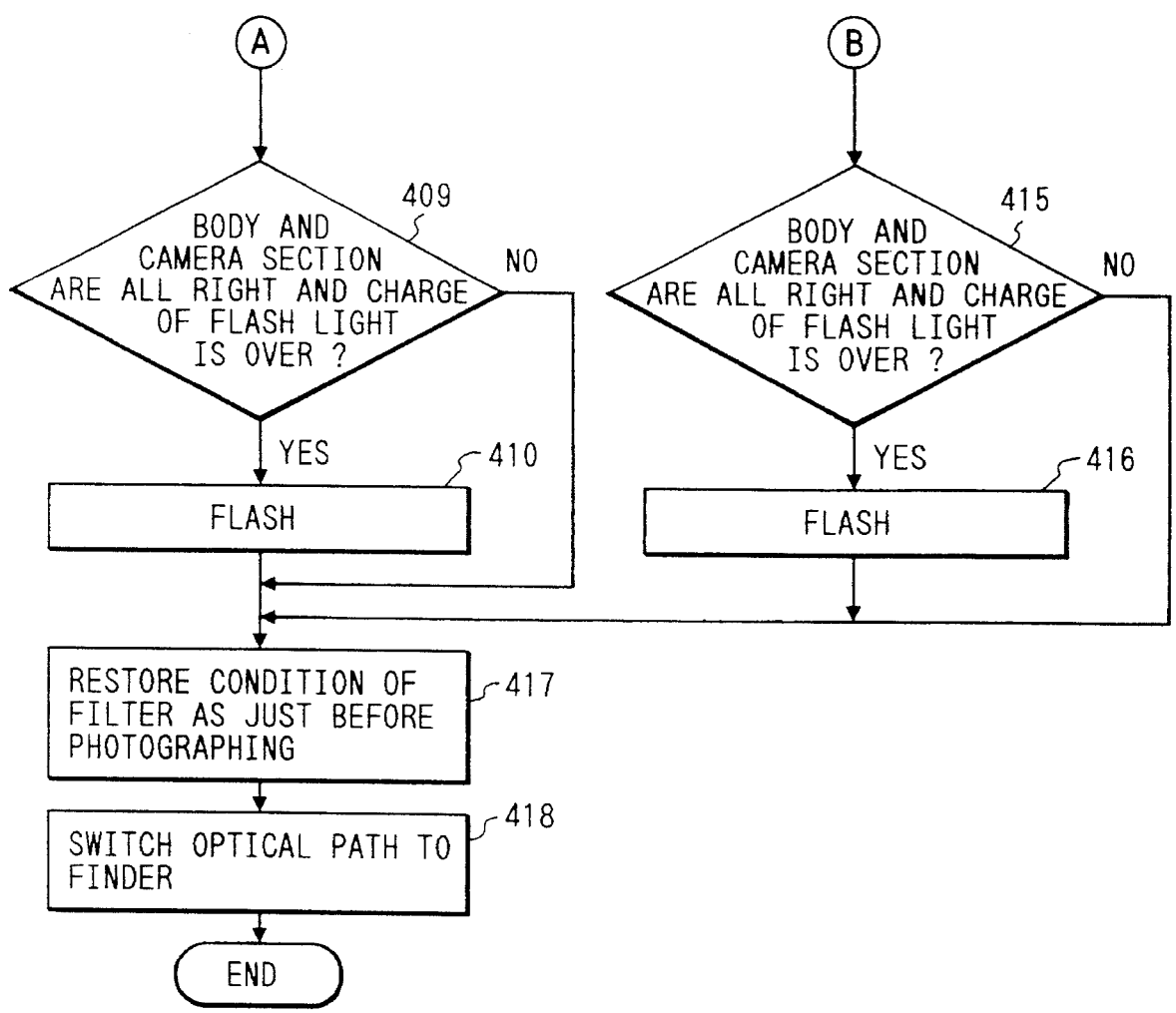
FIG. 5 is a flow chart continued from FIG. 4.

The operation during photographing will now be described with reference to the flow charts of FIGS. 4 and 5.

The first CPU 2 reads the switch of the joy stick 10 (step 401), and judges whether the switch of the joy stick 10 has been depressed (step 402). The first CPU 2 judges whether a predetermined time has passed since the last flashing of the power source 22 for flash light (steps 403). When it is judged that the predetermined time has passed, the state of the camera section 30 selected by the camera selection means 5 and the charged state of the power source 22 for flash light in the power source section 20 are confirmed (step 404).

In this manner, the first CPU 2 confirms the states of the body 1, the power source section 20 and the camera section 30, and when it judges that they are in normal states in which photographing is possible, the first CPU 2 transmits a photographing command, etc. to the third CPU 21 and the second CPU 31.

If the camera section 30 selected by the camera selection means 5 is that mounted on the camera mount 1, the first CPU 2 switches the optical path from the finder to the camera mount 1 (step 405).

When the third CPU 21 receives the photographing command from the first CPU 2, it controls the quantity of flash light and the brightness of the data display section in conformity with the differences in the size of the image of the fundus of the eye on the camera, the photo-taking angle of view, the type of the filter, the diameter of the pupil and the optical path by the type of the camera section, the set value of the film speed, the exposure correction value, etc. so as to be suitable for the camera section 30.

In other words, the first CPU 2 controls the filter in conformity with the type of the film and the photographing condition (step 406).

Thereafter, the first CPU 2 transmits the photographing command to the third CPU 21 of the power source section 20 (step 407) and transmits the photographing command to the camera (step 408).

When the series of operations are completed, it is confirmed that there is no abnormality in the camera section 30, and the completion of the charging of the power source 22 for flash light is confirmed (step 409). If the charging is completed, flash light is emitted (step 410).

Also, when at the step 404, the first CPU 2 judges that the camera 2 is selected by the camera selection means, it switches the optical path from the finder to the camera mount 2 (step 411).

When the third CPU 21 receives the photographing command from the first CPU 2, it controls the quantity of flash light and the brightness of the data display section in conformity with the differences in the size of the image of the fundus of the eye on the camera, the photo-taking angle of view, the type of the filter, the diameter of the pupil and the optical path by the type of the camera section, the set value of the film speed, the exposure correction value, etc. so as to be suitable for the camera section 30.

When the series of operations are completed, it is confirmed that there is no abnormality in the body 1 and the camera section 30, and the completion of the charging of the power source 22 for flash light is confirmed (step 415). If the charging is completed, flash light is emitted (step 416). When the flashing is completed, the filter is restored to the condition as just before photographing (step 417). Thereafter the optical path is switched to the finder (step 418).

In the foregoing description, flash light has been emitted in a predetermined time after the detection of the ON of the joy stick switch, but alternatively, flash light may be emitted upon the x contact signal from the camera section 30.

The operation of the camera section will now be described with reference to the flow charts of FIGS. 6 and 7.

Referring to FIG. 6 which is a flow chart of an instant camera, the second CPU 31 reads the conditions of the camera (film is not inserted, film is inserted but not loaded, film has an unexposed portion, the winding of film has been completed, the type of film is color film, monochromatic film, for color photographing or for fluorescent photographing, etc.) (step 501). When the reading is completed, whether a command for reading out condition data has been received from the first CPU 2 is judged (step 502). If the command has been received, the types and conditions of the camera and film are transmitted to the first CPU 2 of the body 1 (step 503). When at the step 502, it is judged that the command is not received, whether the photographing command has been received is judged with it being understood that the first CPU 2 has already received and acknowledged the conditions of the camera (step 504). If the photographing command has been received, whether the film is loaded is judged (step 505). If the film is not loaded, the first dark slide of the film pack is discharged (step 506). If the film is loaded, an electronic shutter is opened to expose the film (step 507). After the film has been exposed for a predetermined time, the electronic shutter is closed (step 508). Thereafter the exposed film is discharged (step 509).

Referring to FIG. 7 which is a flow chart illustrating the operation of a 35 mm camera, the second CPU 31 reads the conditions of the camera (step 601). When the reading is completed, whether a command for reading out the condition data has been received from the first CPU 2 is judged (step 602). If the command has been received, the types and conditions of the camera and film are transmitted to the first CPU 2 of the body 1 (step 603). When at the step 502, it is judged that the command is not received, whether a photographing command has been received is judged with it being understood that the first CPU 2 has already received and acknowledged the conditions of the camera (step 604). If the photographing command has been received, whether the film is loaded is judged (step 605). If the film is not loaded, the film is loaded (step 606). If the film is loaded, a shutter is opened (step 607), and after a predetermined time has passed, the shutter is closed (step 608). The closing of the shutter is confirmed and the winding of the film is started (step 609). The state of the film winding is read so as to detect the film end (step 610). When the film end is detected, the winding of the film is stopped (step 611).

As shown in the above-described embodiment, the body and the camera section exchange signals therebetween by seven contacts and therefore, the camera to be added later can be connected if adjusted to the interface specification thereof.

The correspondence of an electronic still camera section will hereinafter be described as an example.

As previously described, the body 1 and the camera section 30 exchange signals therebetween by seven contacts (they also exchange the sensitivity of the solid state image pickup element of the camera section 30 as converted into film speed). The body 1 transmits a photographing command to the electronic still camera section 30 during photographing. The body 1 switches the optical path to the electronic still camera section (the optical path has already been switched when it is utilized as an electronic finder). The second CPU 31 of the camera section 30 puts out a signal for taking synchronism with the electronic still camera to take the timing of flashing with the video signal of the electronic still camera. The electronic still camera which has received the synchronizing signal returns a signal at the timing at which the video signal causes the flash device to emit light. That signal is returned as the x contact signal to the body 1 through the second CPU 31 or directly, whereby the flash device is caused to emit light.

In the electronic still camera, as compared with a 35 mm camera and an instant camera, the sensitivity of the solid state image pickup element seems to be relatively high because the exposed area is small. During the flashing of the flash device, excessive exposure may be provided because the limit of the control of flash light is exceeded in the power source section 20 for flash light in an eye fundus camera designed for a 35 mm camera or an instant camera. Accordingly, an ND filter must be inserted into the optical path near the front face of the solid state image pickup element of the electronic still camera. When this filter is to be manually inserted, a line for outputting a filter condition signal from the camera section 30 to the body 1 becomes necessary. This is for the purpose of giving warning, prohibiting the flashing of the flash device and discontinuing photographing when this filter is not inserted during photographing. To automatically insert and discharge the ND filter during photographing, an input line for driving the ND filter becomes necessary. This poses a problem as to whether that signal is compatible with the conventional signal, and when it is not compatible, an inherent signal will have to be provided.

Since in the embodiment of the present invention, the body 1 and the camera section 30 exchange signals therebetween by seven contacts, it will become possible to connect the camera section if it is adjusted to the interface specification thereof. When the ND filter is to be manually inserted and discharged, the condition signal of the ND filter can be arranged in addition to the conventional condition signal of the camera section 30 and in accordance therewith, that signal can simply be output from the camera section 30 to the body 1.

When the ND filter is to be automatically inserted and discharged, the second CPU 31 of the camera section 30 controls the insertion and the discharge of the ND filter after photographing in accordance with an ND filter insertion command from the body.

In this manner, without remodeling the base plate of the body 1, a new camera section can be easily added by changing the program at the most.

Description will now be made of a case where a plurality of finders are used.

Finder selection means 6 for an eyepiece finder and an electronic finder is provided. Alternatively, a function is added to the camera selection means 5 so that where the camera selected by the camera selection means 5 is a television camera, the television camera may be used as an electronic finder.

Provision is also made of sensitivity difference setting means for setting the sensitivity difference between the eyepiece finder and the television camera section when the television camera section is used as the electronic finder.

When the electronic finder is selected, the quantity of observation illumination light is controlled in accordance with the value of the switch thereof.

As an example, description will hereinafter be made of a case where a 35 mm camera section is mounted on the camera mount 1, a television camera section is mounted on the camera mount 2 and the camera selection means 5 is used also as the finder selection means 6.

The camera section 30 is made intelligent.

The eye fundus camera body 1 outputs a command for reading out conditions to the camera section 30. The camera section 30 receives it, and thereafter responds to the conditions. Accordingly, the body acknowledges that the 35 mm camera section is mounted on the camera mount 1 and the television camera section is mounted on the camera mount 2.

When the camera selection means selects the camera mount 1, the camera mounted thereon is a 35 mm camera and therefore it cannot be utilized as an electronic finder and thus, the optical path is switched to the eyepiece finder. As regards the quantity of observation illumination light in this state, the examiner manipulates the volume of the observation light quantity setting device 8 under conditions such as the type of the angle of view setting means 11, the type of the filter and the kind of the diameter of pupil so as to be suited for the examiner to observe the image of the fundus of the eye with his naked eye.

When the examiner varies the angle of view, the filter, the diameter of pupil, etc., the third CPU 21 of the power source section 20 controls the power source for observation light and varies the quantity of observation illumination light to thereby adjust it so that the brightness of the image of the fundus of the eye seen through the eyepiece finder may not vary.

When the camera selection means 5 selects the camera mount 2, the camera mounted thereon is a television camera and therefore, it can be utilized as an electronic finder. Accordingly, the body 1 switches the optical path from the eyepiece finder to the electronic finder. The optical path is switched by driving a quick return mirror. The quick return mirror is fixed so as to fix the optical path on the electronic finder side of the camera 2 while the camera selection means 5 is on the camera mount 2 side.

Means for setting the sensitivity difference from the eyepiece finder when the electronic finder is used is provided in the television camera section. The state of the sensitivity difference setting means is pre-transmitted from the camera section 30 to the body 1. It is further transmitted from the body 1 to the power source section 20. The sensitivity difference between the eyepiece finder and the electronic finder is added to the conventional conditions under which the third CPU 21 of the power source section 20 determines the quantity of observation illumination light (the volume of the observation light quantity setting device, the types of the angle of view setting means 11 and the filter, the kind of the diameter of pupil, etc.).

Where the means for setting the sensitivity difference of the electronic finder is comprised of three bits, the sensitivity difference can be adjusted at seven stages of 1 to 7. Assuming that when for example, the degree indicated by the sensitivity difference setting means is 4 when the optical path is switched from the eyepiece finder to the electronic finder, there is no sensitivity difference between the eyepiece finder and the electronic finder, it is not necessary to vary the quantity of observation illumination light. Also, when the degree indicated by the sensitivity difference setting means is 5–7, adjustment is made so as to increase the quantity of observation illumination light. On the other hand, when the degree indicated by the sensitivity difference setting means is 1–3, adjustment is made so as to decrease the quantity of observation illumination light. The adjustment can be accomplished by how much adjusting the output voltage of a power source for an observation illumination lamp at one stage of the degrees indicated, or varying the resistance value between the power source and the lamp while keeping the output of the power source constant.

What is claimed is:

1. In an ophthalmic instrument having a plurality of finder systems, which function differently from each other, for observing an examinee's eye illuminated by light from an observation illumination lamp, the improvement comprising:

an optical path switching device for selectively guiding the light from said illuminated examinee's eye to one of said plurality of finder systems;

a sensitivity difference setting device for setting a sensitivity difference between finder systems of said plurality; and a light quantity setting device for adjusting the quantity of light provided from said observation illumination lamp based on said sensitivity difference.

2. An ophthalmic instrument according to claim 1, wherein said light quantity setting device adjusts said quantity of light such that the brightness of the observed examinee's eye is substantially the same for each of said plurality of finder system.

3. An ophthalmic instrument according to claim 1, wherein said plurality of finder system include an eyepiece finder and an electronic finder.

* * * * *